(12) United States Patent
Geurts (10) Patent No.: US 7,262,835 B2
(45) Date of Patent: Aug. 28, 2007

(54) FLUORESCENCE MEASURING DEVICE FOR GEMSTONES

(75) Inventor: Ronald Geurts, Hove (BE)

(73) Assignee: Gemological Institute of America, Inc., Carlsbad, CA (US)

( * ) Notice: Subject to any disclaimer, the term of this patent is extended or adjusted under 35 U.S.C. 154(b) by 0 days.

(21) Appl. No.: 11/388,387

(22) Filed: Mar. 23, 2006

(65) Prior Publication Data
US 2006/0164625 A1 Jul. 27, 2006

(51) Int. Cl.
*G01N 21/00* (2006.01)
(52) U.S. Cl. ........................................ 356/30
(58) Field of Classification Search ............... 356/30
See application file for complete search history.

(56) References Cited

U.S. PATENT DOCUMENTS

| | | | |
|---|---|---|---|
| 4,461,568 A | 7/1984 | Welbourn et al. |
| 4,508,449 A | 4/1985 | Okazaki |
| 5,118,181 A | 6/1992 | Yifrach et al. |
| 5,801,819 A | 9/1998 | Spear et al. |
| 5,811,824 A | 9/1998 | Smith et al. |
| 5,835,205 A | 11/1998 | Hunter et al. |
| 5,883,389 A | 3/1999 | Spear et al. |
| 5,955,735 A | 9/1999 | Coleman |
| 6,014,208 A | 1/2000 | Welbourn et al. |
| 6,239,867 B1 | 5/2001 | Aggarwal |
| 6,331,708 B2 | 12/2001 | Smith |
| 6,473,164 B1 | 10/2002 | De Jong et al. |
| 2005/0151959 A1* | 7/2005 | Geurts ..................... 356/30 |

OTHER PUBLICATIONS

International Search Report for PCT Application No. PCT/US05/01535, mailed Jul. 18, 2005.

* cited by examiner

*Primary Examiner*—Roy M. Punnoose
(74) *Attorney, Agent, or Firm*—DLA Piper US LLP (57) ABSTRACT

A gemstone fluorescence measuring device according to the invention generally includes an ultraviolet ("UV") emission chamber, a UV radiation source, and a light meter assembly. The UV radiation source includes an upper light emitting diode ("LED") and a lower LED that radiate a gemstone under test from both above and below the gemstone. The UV radiation source provides both trans-radiation and direct radiation to the gemstone, and the UV radiation source has an adjustable intensity, thus facilitating calibration of the fluorescence measuring device. The light meter assembly includes a light detector that detects the visible light emitted from the gemstone under test in response to the UV radiation. The light detector is configured to simulate the spectral characteristics of the human eye. The fluorescence measuring device converts the measured visible light into a numerical lux reading, which can then be converted into a fluorescence grade for the gemstone under test.

10 Claims, 5 Drawing Sheets

FLUORESCENCE MEASURING DEVICE FOR GEMSTONES

FIELD OF THE INVENTION

The present invention relates generally to gemological instrumentation. More particularly, the present invention relates to instrumentation for measuring the fluorescence of gemstones such as diamonds.

BACKGROUND OF THE INVENTION

Gemstones such as diamonds are traditionally graded based upon their appearance characteristics. For example, the following diamond qualities are typically included in standard grading reports: shape; weight (carat); clarity; color; fluorescence; and cut characteristics. In the context of gemstone analysis, "fluorescence" refers to the emission of visible light from a gemstone while exposed to ultraviolet ("UV") radiation. The fluorescence of diamonds is usually graded using the following classifications: None; Faint; Medium; Strong; and Very Strong.

Traditionally, diamonds are graded by human inspectors who have been trained to identify and quantify the visible characteristics (with or without the aid of test equipment). Human inspectors grade the fluorescence of a diamond (and other gems) by illuminating the diamond with a controlled UV light source and observing the visible light emitted from the diamond. The human inspectors classify the diamond according to the intensity of the emitted visible light. In a diamond grading lab environment, technicians usually employ fluorescence reference "master stones" to improve consistency. Nevertheless, due to the inherently subjective nature of human fluorescence grading, some diamonds may be misclassified, especially if the appearance of a diamond is on the borderline between classifications. Furthermore, the same human grader may classify a diamond differently depending upon a number of factors such as: his or her level of fatigue; the environmental conditions; the size and/or cut of the diamond; the color of the fluorescence; the orientation of the observation; the instability of the light source; and the like.

The prior art includes a number of instruments designed to "automate" some of the gemstone grading processes by removing the human component. These instruments serve as a confirmation of the human grading process, and are not intended to completely replace the human grading procedure. The prior art, however, does not include an inexpensive, simple to operate, diamond fluorescence measuring device that is designed to electronically measure the fluorescence of a diamond by illuminating the diamond with a stable UV light source. In contrast, sophisticated and expensive fluorescence measuring equipment exists for other uses such as fluorescence spectrophotometry, x-ray, and microscopy applications—gemstone fluorescence grading does not require such sophisticated and expensive equipment.

BRIEF SUMMARY OF THE INVENTION

A fluorescence measuring device for gemstones is described herein. A fluorescence measuring device configured in accordance with the invention employs a stable and adjustable UV radiation or light source. In the example embodiment described herein, the UV source includes two light emitting diodes ("LEDs") that are substantially aligned with each other. A gemstone such as a diamond is positioned between the two LEDs, and the LEDs are activated to provide a combination of trans-radiation (i.e., radiation through the object) and direct radiation (i.e., radiation toward the object) of the gemstone. The fluorescence measuring device includes a light detector or light meter positioned to measure the visible light emitted from the gemstone. The measured quantity can then be processed and converted into an alphanumeric grade, a category, or other suitable processing unit.

The above and other aspects of the present invention may be carried out in one form by a fluorescence measuring device for a gemstone under test. The fluorescence measuring device includes a UV radiation source configured to provide trans-radiation and direct radiation to the gemstone under test, and a light detector positioned proximate the gemstone under test. The light detector is configured to detect visible light emitted from the gemstone under test in reaction to the applied UV radiation.

BRIEF DESCRIPTION OF THE DRAWINGS

A more complete understanding of the present invention may be derived by referring to the detailed description and claims when considered in conjunction with the following Figures, wherein like reference numbers refer to similar elements throughout the Figures.

DETAILED DESCRIPTION OF A PREFERRED EMBODIMENT

The present invention may be described herein in terms of functional block components and various processing steps. It should be appreciated that such functional blocks may be realized by any number of hardware, software, and/or firmware components configured to perform the specified functions. For example, the present invention may employ various integrated circuit components, e.g., memory elements, digital signal processing elements, logic elements, look-up tables, and the like, which may carry out a variety of functions under the control of one or more microprocessors or other control devices. In addition, those skilled in the art will appreciate that the present invention may be realized in any number of practical implementations and that the system shown and described herein is merely one exemplary application for the invention.

It should be appreciated that the particular implementations shown and described herein are illustrative of the invention and its best mode and are not intended to otherwise limit the scope of the invention in any way. Indeed, for the sake of brevity, conventional aspects of UV radiation generation, LED technology, light detection and measurement, gemstone grading techniques, and other features or functions of the systems (and the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical embodiment.

Figure 1:
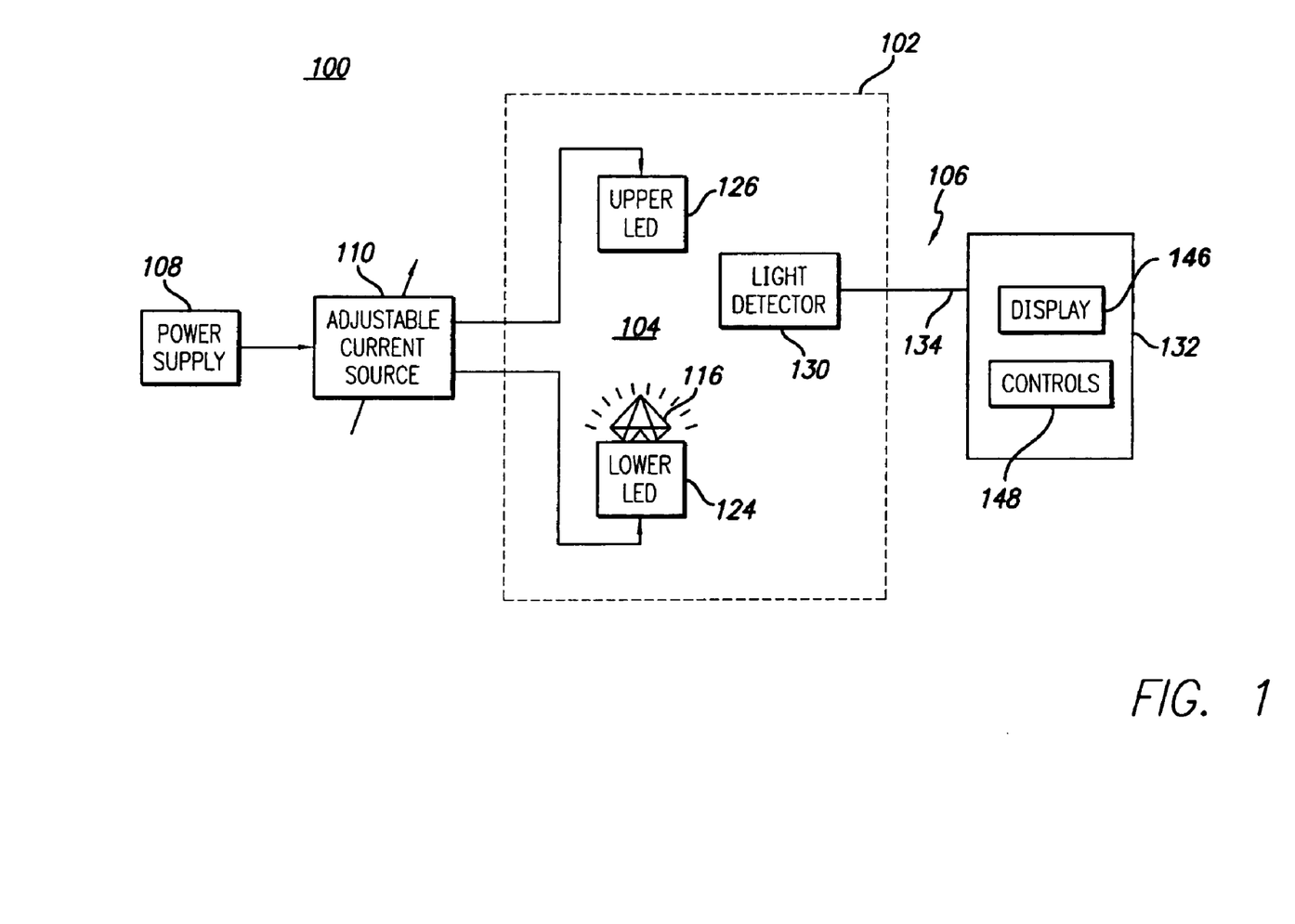
FIG. 1 is a schematic representation of a fluorescence measuring device for gemstones.
Figure 5:
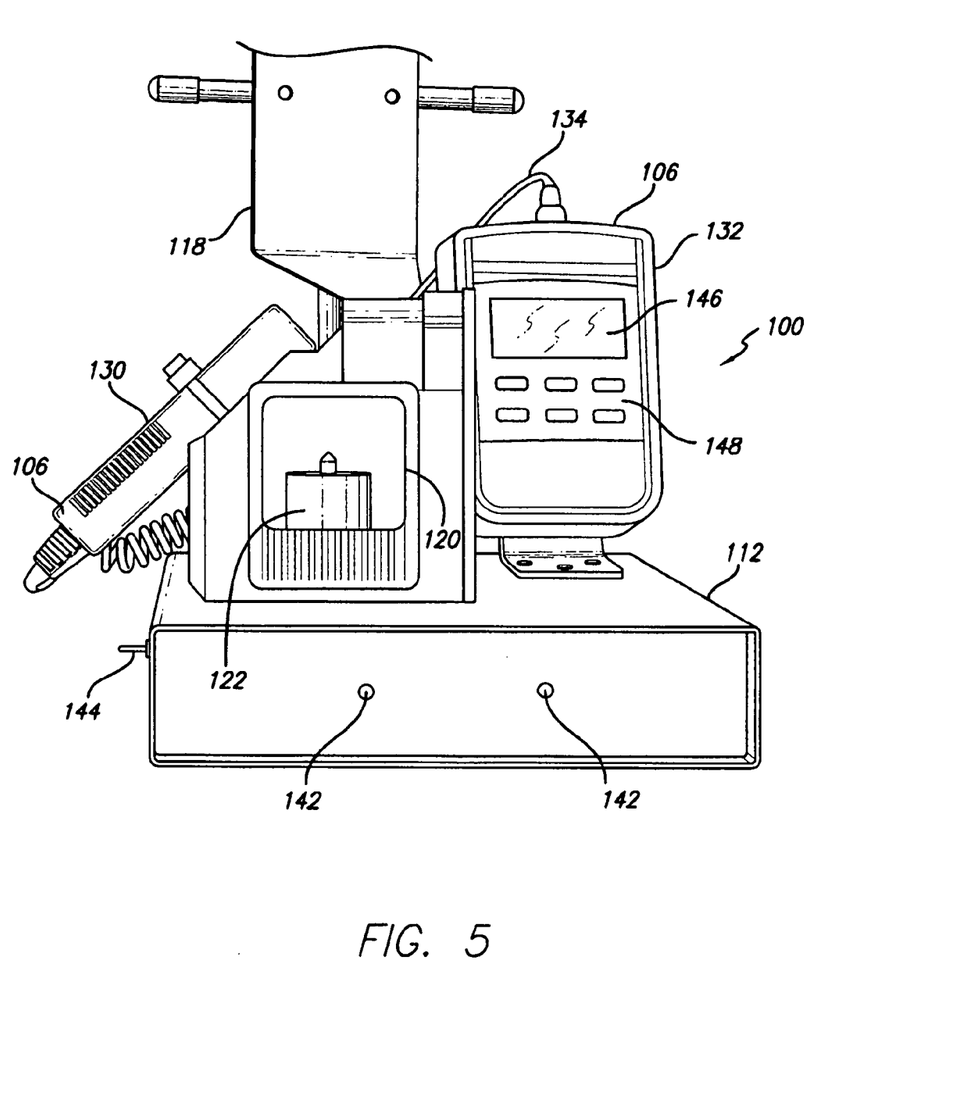
FIG. 5 is a front perspective view of a practical embodiment of a fluorescence measuring device for gemstones.
Figure 6:
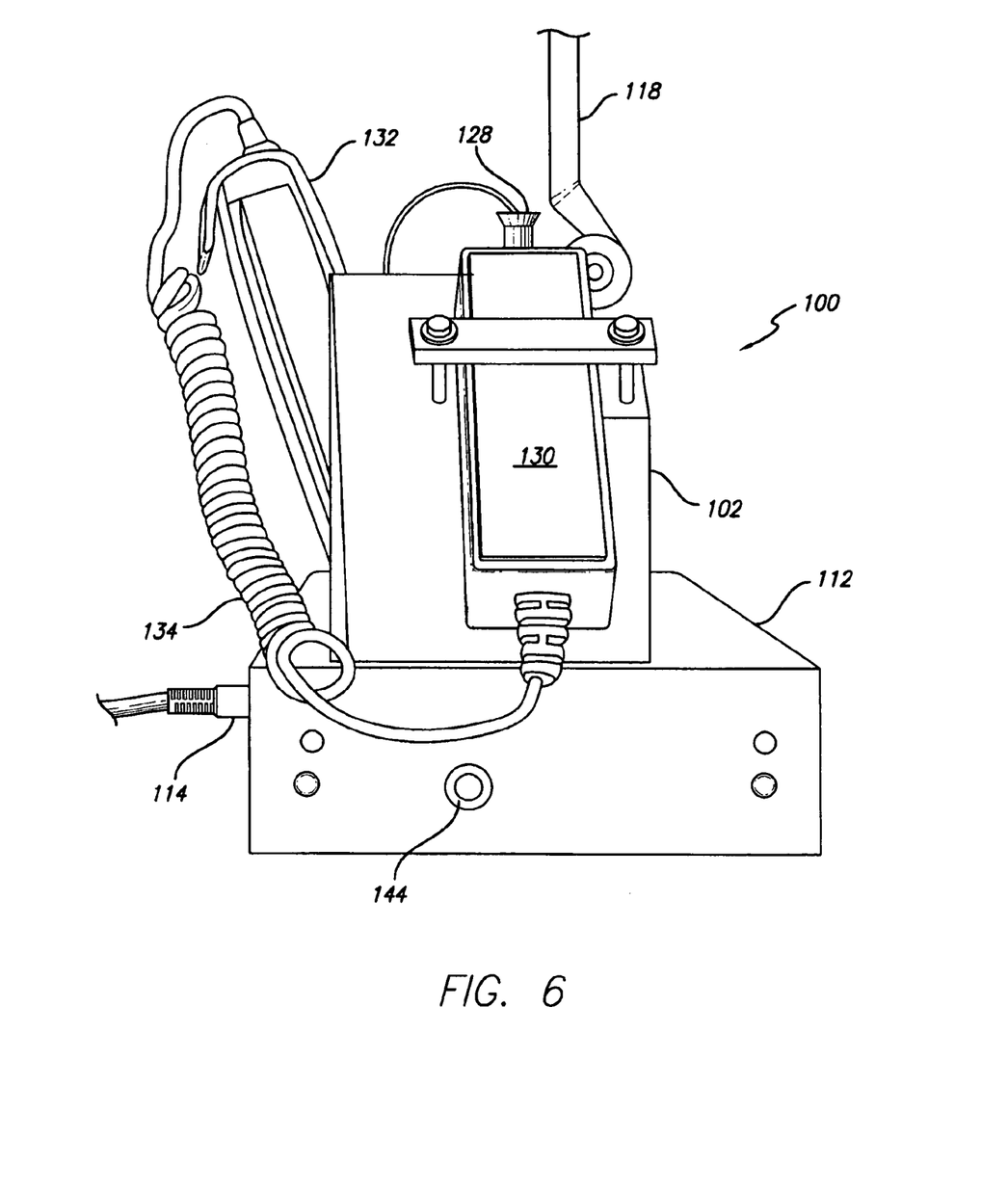
FIG. 6 is a side perspective view of the fluorescence measuring device shown in FIG. 5.

FIG. 1 is a schematic representation of a gemstone fluorescence measuring device 100 configured in accordance with the present invention. FIG. 5 is a front perspective view of one practical embodiment of fluorescence measuring device 100, and FIG. 6 is a side perspective view of the fluorescence measuring device 100 shown in FIG. 5. Fluorescence measuring device 100 is suitably configured to measure the fluorescence of gemstones, e.g., diamonds. For convenience, the following description of fluorescence measuring device 100 refers to the measurement and grading of diamonds. The invention, however, is not limited to diamond applications.

Fluorescence measuring device 100 generally includes an emission chamber 102, a UV radiation source 104, a light meter assembly 106, a power supply 108, and an adjustable current source 110. The example embodiment depicted in FIGS. 5 and 6 includes a base housing 112 that serves as the foundation for fluorescence measuring device 100. Base housing 112 can be formed from metal, plastic, or any suitable material. Base housing 112 serves as a housing for power supply circuitry, adjustable current source 110, and, if necessary, other circuits, components, and/or functional elements of fluorescence measuring device 100 (these components are hidden from view in FIGS. 5 and 6). Base housing 112 also serves as a mounting platform for emission chamber 102 and light meter assembly 106, as illustrated in FIGS. 5 and 6.

One embodiment of fluorescence measuring device 100 receives its power from a standard 120 volt or 240 volt AC line. The example embodiment utilizes an AC/DC adapter (not shown) that converts the AC power into 12 volts DC. FIG. 6 depicts an end 114 of the AC/DC adapter attached to a suitable receptacle or plug mounted to base housing 112. In this embodiment, power supply 108 is realized as the AC/DC adapter. In other embodiments, power supply 108 may be incorporated into fluorescence measuring device 100 itself, e.g., as circuitry located within base housing 112. As described in more detail below, power supply 108 provides power to UV radiation source 104 and, if necessary, to other components of fluorescence measuring device 100. Although not shown, fluorescence measuring device 100 includes a main on/of switch, which may be mounted on base housing 112.

Emission chamber 102 is configured to accommodate a diamond under test 116. Emission chamber 102 can be formed from metal, plastic, or any suitable opaque material. In the example embodiment, emission chamber 102 is machined from black plastic. Emission chamber 102 includes a hinged access door 118 that covers an access window 120 when closed. When open, access door 118 facilitates the placement and removal of the diamond under test 116. The access window 120 is preferably sized such that positioning of the diamond under test 116 can be accomplished using ambient light that enters emission chamber 102. In the example embodiment, access window 120 has the following approximate dimensions: 1.75 inches by 1.75 inches. When closed, access door 118 "seals" emission chamber 102 and prevents ambient light from entering the interior of emission chamber 102. After access door 118 is lowered into the closed position, the force of gravity keeps it in place.

Figure 3:
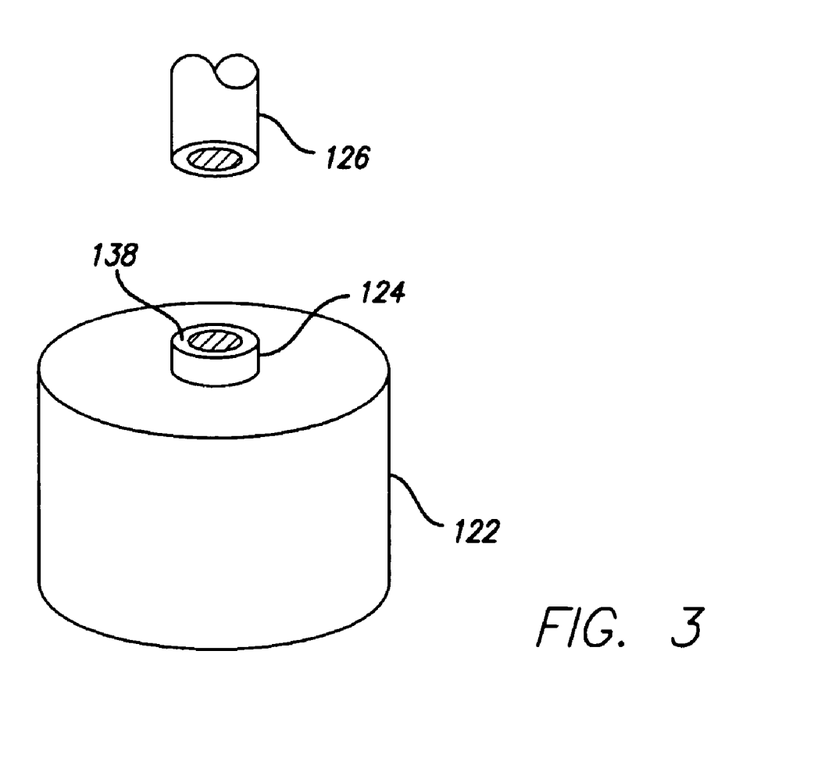
FIG. 3 is a perspective view of a gemstone pedestal and LEDs of an example fluorescence measuring device.
Figure 4:
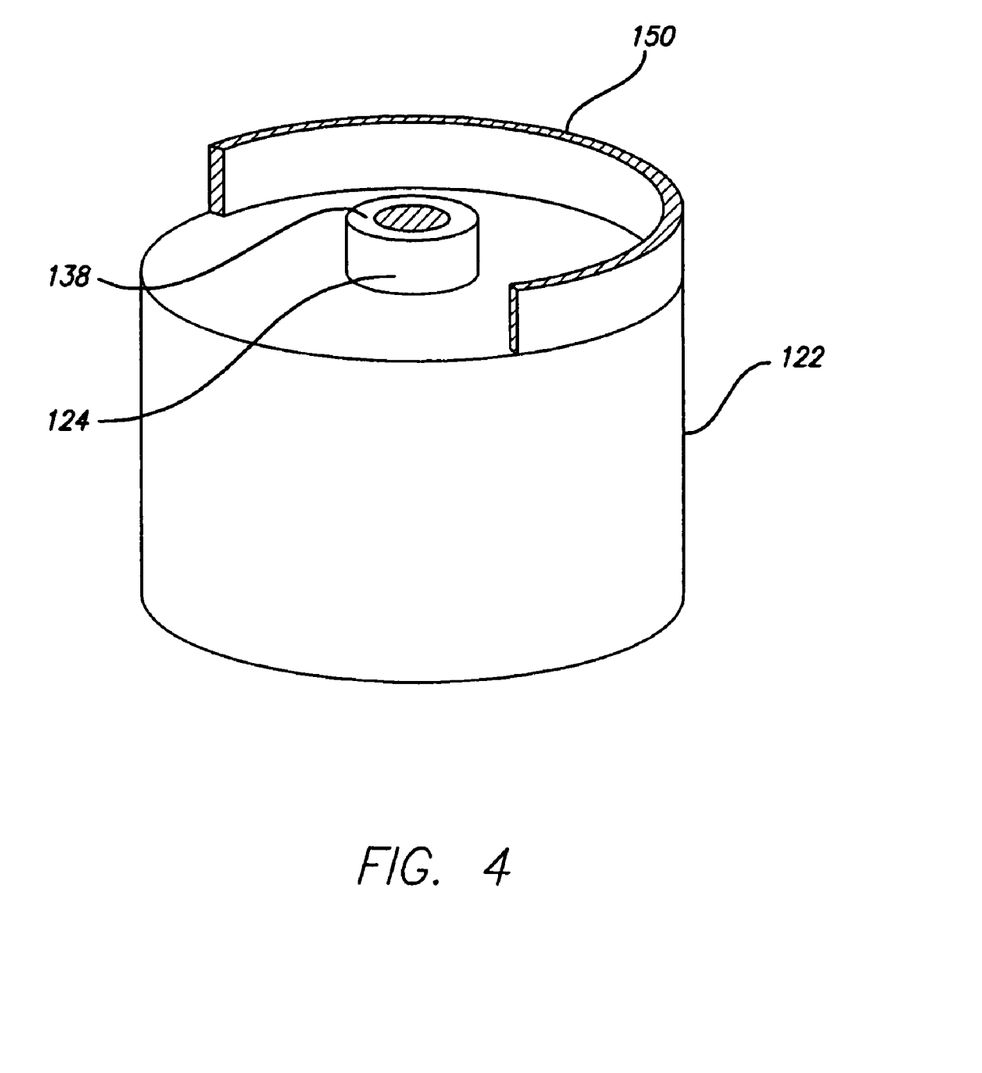
FIG. 4 is a perspective view of the gemstone pedestal shown in FIG. 3, and a reflector positioned upon the gemstone pedestal.

As shown in FIG. 5, fluorescence measuring device 100 may include a pedestal 122 located within the interior of emission chamber 102. Pedestal 122 is also depicted in FIGS. 3 and 4. In the example embodiment, pedestal 122 is generally cylindrical in shape and its circumference follows the inner wall contour of emission chamber 102. Pedestal 122 provides a raised level for the positioning of the diamond under test 116, thus making it easier to insert and remove the diamond from the interior of emission chamber 102. The height of pedestal 122 is selected in accordance with the desired radiation and light detection characteristics of fluorescence measuring device 100 (described in more detail below). In the example embodiment, pedestal 122 is approximately 0.05 to 0.10 inches in height. Pedestal 122 also functions as a structural mount for a portion of UV radiation source 104 (in the example embodiment, a UV LED is mounted within pedestal 122).

In accordance with a practical embodiment, UV radiation source 104 comprises a plurality of LEDs. In the preferred embodiment, UV radiation source 104 includes a lower LED 124 and an upper LED 126. Lower LED 124 is centrally mounted within pedestal 122 such that the respective UV radiation is emitted upward. Upper LED 126 is mounted within the upper portion of emission chamber 102 such that the respective UV radiation is emitted downward. The tip of upper LED 126 is shown in FIG. 5, and a receptacle 128 for upper LED 126 is shown in FIG. 6. In operation, the UV radiation emitted from LEDs 124/126 is maintained within emission chamber 102.

Light meter assembly 106 includes a light detector 130, a controller-processor 132, and a cable 134 for coupling light detector 130 to controller-processor 132. At least a portion of light detector 130 is positioned within the interior of emission chamber 102 and proximate the diamond under test 116 (as schematically represented in FIG. 1 and as shown in FIG. 5). In FIG. 5, the portion of light detector 130 located within emission chamber 102 is shown at the upper left corner of access window 120. As described in more detail below, light detector 130 is configured to detect visible light emitted from the diamond under test 116 in reaction to UV radiation applied to the diamond under test 116.

To facilitate accurate fluorescence measurements, the interior of emission chamber 102, pedestal 122, and other features of fluorescence measuring device 100 located within emission chamber 102 have non-reflective surfaces. For example, the interior of emission chamber 102 and pedestal 122 can be coated, anodized, plated, or otherwise colored flat black to reduce the amount of reflected light detected by light meter assembly 106.

Figure 2:
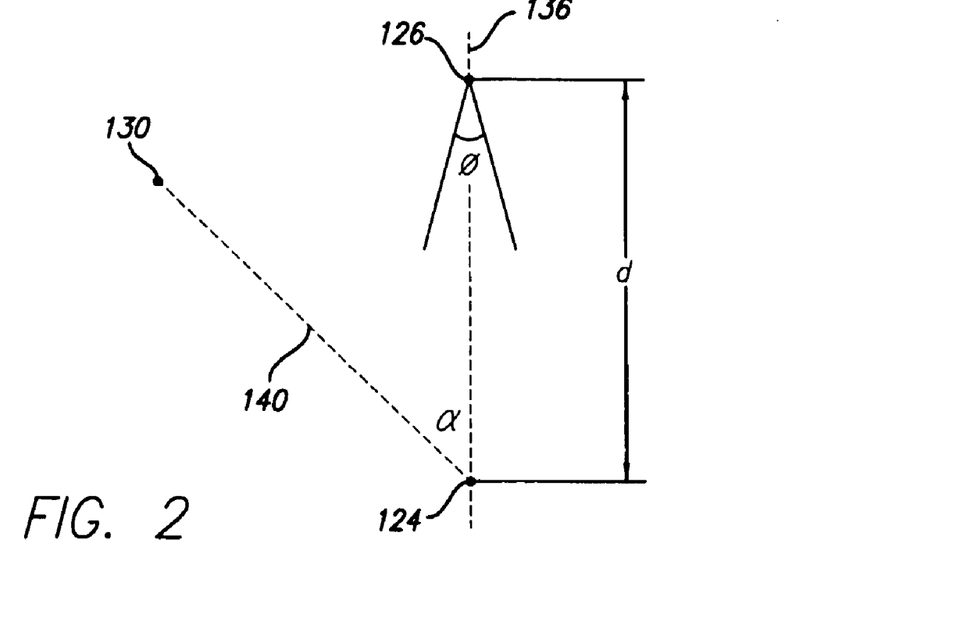
FIG. 2 is a diagram that illustrates the geometry of LEDs and a light detector of an example fluorescence measuring device.

FIG. 2 is a diagram that illustrates the relative geometry of the LEDs 124/126 and light detector 130 of fluorescence measuring device 100. For purposes of FIG. 2 and the following description, LEDs 124/126 and light detector 130 are depicted as points. In practice, LEDs 124/126 will emit UV radiation from a small area, and light detector 130 will receive visible light over a small area. The representation of these components as points simplifies the description of the geometry.

Upper LED 126 and lower LED 124 share a common emission axis 136 (depicted as a vertical dashed line in FIG. 2). In this regard, upper LED 126 emits UV radiation along emission axis 136 toward lower LED 124, and lower LED 124 emits UV radiation along emission axis 136 toward upper LED 126. In other words, the LEDs 124/126 are vertically aligned in the example embodiment. Furthermore, in an actual working embodiment, each of the LEDs emits a relatively narrow, conically shaped, UV radiation beam that forms an angle θ (as shown for LED 126 in FIG. 2). In accordance with one preferred embodiment, the angle θ equals approximately 10–20 degrees. This relatively small angle is desirable for having a maximum reaction in relation to the total produced UV radiation by the LED and because it facilitates initial adjustment and calibration of the radiation source.

The emission points of LEDs 124/126 are separated by a distance d, as shown in FIG. 2. In the example embodiment, d falls within the range of 0.6 to 0.8 inches. The distance d is selected according to the desired intensity of the visible light emitted from the diamond under test 116. For example, if higher intensity is desired, then the distance d can be reduced. Although the distance d is fixed in the example embodiment, it may be adjustable to provide an additional degree of freedom to fluorescence measuring device 100.

In the example embodiment, lower LED 124 includes a mounting surface 138 (see FIG. 3) configured to accommodate the diamond under test 116. In the practical embodiment, lower LED 124 is generally cylindrical in shape with a relatively flat perimeter lip that functions as mounting surface 138. Optionally, fluorescence measuring device 100 may employ a protective film or tape between lower LED 124 and the diamond under test 116. In operation, the diamond under test 116 is placed onto mounting surface 138 in a table-down position, as shown in FIG. 1. Accordingly, mounting surface 138 is located between upper LED 126 and lower LED 124. Fluorescence measuring device 100 may alternatively include structure (not shown) for providing a mounting surface distinct from lower LED 124. For example, a clear plate or window positioned between LEDs 124/126 can be employed.

Referring again to FIG. 2, light detector 130 is preferably located such that its "line of sight" 140 to the diamond under test 116 (which, for the sake of simplicity, corresponds to the position of lower LED 124 in FIG. 2) forms an angle α of approximately 45 degrees with emission axis 136. The 45 degree angle simulates the viewing angle commonly used by human inspectors when measuring the fluorescence of diamonds.

UV radiation source 104 is configured to provide trans-radiation and direct radiation to the diamond under test 116. In this context, trans-radiation refers to radiation through the diamond under test 116, while direct radiation refers to radiation on or towards the diamond under test 116. In the example embodiment, upper LED 126 contributes significantly to the direct radiation, while lower LED 124 contributes significantly to the trans-radiation. This combined radiation of the diamond under test 116 results in consistent test conditions, stable UV radiation, and repeatable fluorescence measurements, and allows the measurement of opaque diamonds or transparent diamonds that react only superficially to UV radiation and do not allow the UV radiation to penetrate substantially into the diamond.

In the practical embodiment, LEDs 124/126 are identical. LEDs 124/126 have the following characteristics, which are desirable for use with fluorescence measuring device 100: visible light filtering such that the emitted radiation is pure UV radiation; peak output intensity around 370 nm wavelength (i.e., the LEDs provide "long wave" UV radiation); package diameter equals 5.6 mm. LEDs 124/126 can be realized by the commercially available LED model number RLT370-10, available from Roithner Lasertechnik of Vienna, Austria. Of course, other commercially available LED emitters may be suitable for use with fluorescence measuring device 100, and LEDs having different operating characteristics can be used to suit the needs of different practical applications.

Base housing 112 may include indicator or status lights 142 corresponding to LEDs 124/126. Status lights 142 indicate whether the respective LEDs 124/126 are in operation. Status lights 142, which may be driven by power supply 108, monitor the current to each of the LEDs 124/126 and indicate failure when they are not lit.

The UV radiation source 104 is adjustable to facilitate calibration and variation of the amount of UV radiation applied to the diamond under test 116. In practice, UV radiation source 104 is connected to adjustable current source 110 (see FIG. 1), which regulates the drive current to LEDs 124/126. In turn, the output power of LEDs 124/126, which is dictated by the drive current, is adjusted. In the example embodiment, adjustable current source 110 is configured to drive LEDs 124/126 from 80% to 120% of their rated power range. Although not a requirement of the invention, adjustable current source 110 simultaneously adjusts the current to both LEDs 124/126. Concurrent adjustment is desirable to reduce the complexity of the calibration. Alternate embodiments can have each LED 124/126 independently adjustable.

As shown in FIGS. 5 and 6, fluorescence measuring device 100 may employ a user interface element 144 (e.g., a rheostat, a potentiometer, one or more switches, or an electronic controller) for adjusting the output power of UV radiation source 104. In this regard, adjustable current source 110 can be controlled by user interface element 144.

In the context of this description, the UV radiation source 104, the gemstone mounting surface, and adjustable current source 110 form a radiation subsystem. The radiation subsystem can be employed in fluorescence measuring device 100 as shown or in other fluorescence measuring applications.

Light detector 130 includes a correction filter that converts the actual measured values into "human-perceived" values. In other words, light detector 130 is configured such that its spectral response simulates the spectral response of the average human eye. In the practical embodiment, light meter assembly 106 is realized as a commercially available photographer's light meter device. One device suitable for use as light meter assembly 106 is the Mavolux 5032B meter, manufactured by Gossen Foto of Nurnberg, Germany. This meter is a very high resolution meter (resolution of 0.01 lux), which is desirable for use in fluorescence measuring device 100, where low light intensities are measured. In typical diamond fluorescence measurements, light intensities fall within the range of 0.01 and 5 lux.

Light meter assembly 106 is a battery-powered unit having a power supply that is independent of power supply 108. Alternate embodiments may integrate light meter assembly 106 with fluorescence measuring device 100 such that it shares power supply 108.

Controller-processor 132 of light meter assembly 106 includes a display 146 and a control panel 148. Display 146 is an LCD element that provides an alphanumeric reading of the visible light measured by light detector 130. In operation, display 146 indicates the current light intensity, in lux, measured by light detector 130. Control panel 148 provides a user interface with buttons that control the on/off status of light meter assembly 106, the display range, the maximum reading, and other features related to the operation of light meter assembly 106.

Fluorescence measurements using device 100 may be sensitive to the size of the diamond under test 116. Ideally, fluorescence characteristics of a gemstone should be independent of size. The scheme employed by fluorescence measuring device 100—the detection of visible light intensity within emission chamber 102—may require calibration or correction to accommodate the testing of gemstones having a range of sizes. Furthermore, diamonds with uneven fluorescence can give different readings related to the orientation of the diamond on the mounting stage. In this regard, fluorescence measuring device 100 may include a reflector 150 configured for placement within emission chamber 102 (see FIG. 4).

Reflector 150 is formed from a material, such as aluminum, having a reflective surface. When placed within emission chamber 102, reflector 150 functions to reflect some of the visible light, which would otherwise be dissipated within emission chamber 102, toward light detector 130. Fluorescence measuring device 100 may include reflectors 150 having different shapes, sizes, colors, and other reflective characteristics to accommodate different gemstone sizes and/or fluorescence behaviors. The specific height, thickness, curvature profile, radius, and arc length of reflector 150, in addition to the specific positioning of reflector 150 within emission chamber 102, may vary depending upon the type of gemstone being tested, the size of the gemstone, the evenness of fluorescence, and the desired calibration scheme.

As with human fluorescence inspection, master gemstones having known fluorescence characteristics can be used to calibrate fluorescence measuring device 100. In practice, fluorescence measuring device 100 should be calibrated at least once a day using one or more master gemstones. When calibrating fluorescence measuring device 100, the user may need to tune adjustable current source 110 and/or identify one or more reflectors 150 for use during actual testing. Of course, the calibration of fluorescence measuring device 100 can be verified periodically throughout the day. Calibration of fluorescence measuring device 100 can compensate for the aging of LEDs 124/126, scratches or deposits on the emission surfaces of LEDs 124/126, the aging of light meter assembly 106, and the like.

Obtaining a fluorescence measurement of a diamond is relatively straightforward. The access door 118 is opened, and the diamond under test 116 is placed onto mounting surface 138. In practice, the diamond under test 116 is placed table-down onto mounting surface 138 and centered about emission axis 136. Centering is important for consistency in the measurement and the table-down position is the common methodology in fluorescence grading of diamonds. Thereafter, access door 118 is closed and the diamond under test 116 is ready to be radiated. Closure of the access door 118 is a safety measure that prevents UV radiation from accidentally escaping from emission chamber 102 and avoids influences of environmental light incorporated into the measurement.

After engaging the main on/off switch, fluorescence measuring device 100 should be left to warm up for about five minutes. In addition, the on/off button on light meter assembly 106 is switched to the "on" position. The LEDs 124/126 are activated to provide UV radiation to the diamond under test 116. The entire unit can remain on during an extended period (e.g., throughout a day) because of its low power consumption, limited heat production, and very long lifespan of the LEDs. As mentioned above, LEDs 124/126 provide both trans-radiation and direct radiation to the diamond under test 116. In other words, the diamond is radiated from both above and below. As soon as the light meter has been activated, the display 146 should indicate a 0.00 lux reading, as no visible light is recorded in the completely closed emission chamber 102. The light detector 130 detects the visible light emitted from the diamond under test 116 in reaction to the UV radiation. As mentioned above, when excited by UV radiation, certain gemstones fluoresce with visible light. The quantity detected by light detector 130 is processed and converted into a numerical lux reading, which is then rendered on display 146. The lux reading can be recorded by hand or recorded electronically for computer storage and/or processing.

The numerical lux reading for the diamond under test 116 can be converted into a diamond fluorescence grade using any number of fluorescence grading scales recognized in the diamond trade. Thus, the fluorescence of the diamond under test 116 is graded based upon the detected visible light measurement captured by light meter assembly 106. As one practical example, see the following scale, where the measured lux values are representative of a typical application:

| Measured Lux | Fluorescence Grade |
|---|---|
| 0.04 or less | None |
| 0.05 to 0.14 | Faint |
| 0.15 to 0.44 | Medium |
| 0.45 to 1.34 | Strong |
| greater than 1.35 | Very Strong |

Therefore, fluorescence measuring device 100 can be used to verify the fluorescence grade of a human diamond inspector or to independently grade the fluorescence of a diamond. Fluorescence measuring device 100 removes the human component while simulating the human observation conditions traditionally associated with fluorescence grading.

The present invention has been described above with reference to a preferred embodiment. However, those skilled in the art having read this disclosure will recognize that changes and modifications may be made to the preferred embodiment without departing from the scope of the present invention. These and other changes or modifications are intended to be included within the scope of the present invention, as expressed in the following claims.

What is claimed is:

1. A fluorescence measuring device for a gemstone under test, said fluorescence measuring device comprising:
    an ultraviolet ("UV") radiation source configured to provide radiation to the gemstone under test; and
    a light detector positioned proximate the gemstone under test, said light detector being configured to measure directly the intensity of visible light emitted from the gemstone under test in reaction to UV radiation applied to the gemstone under test.

2. A fluorescence measuring device according to claim 1, wherein said UV radiation source comprises a light emitting diode ("LED").

3. A fluorescence measuring device according to claim 2, further comprising a user interface element for adjusting the output power of said LED.

4. A fluorescence measuring device according to claim 3, wherein said user interface element controls the current applied to said LED.

5. A fluorescence measuring device according to claim 1, wherein said light detector is configured such that its spectral response simulates the spectral response of the human eye.

6. A fluorescence measuring device according to claim 1, wherein said light detector is a light meter device.

7. A fluorescence measurement method for gemstones, said method comprising:
    radiating a gemstone under test with ultraviolet ("UV") radiation;
    measuring directly the intensity of visible light emitted from the gemstone under test in reaction to UV radiation applied to the gemstone under test, resulting in a detected visible light measurement; and
    grading fluorescence of the gemstone under test based upon the detected visible light measurement.

8. A method according to claim 7, wherein said radiating step radiates the gemstone under test with a UV radiation source in a closed emission chamber that has substantially no visible light except for the visible light emitted from the gemstone under test in reaction to UV radiation.

9. A method according to claim 7, wherein said measuring step comprises measuring with a light meter device the visible light emitted from the gemstone under test in reaction to UV radiation.

10. A method according to claim 9, further including the step of displaying a current light intensity, in lux, measured by the light meter in the measuring step.

* * * * *